United States Patent [19]

Griat et al.

[11] Patent Number: 5,171,577
[45] Date of Patent: Dec. 15, 1992

[54] PROCESS FOR THE PREPARATION OF FOAMS WHICH CAN BE USED IN THE COSMETICS AND PHARMACEUTICAL FIELD AND FOAMS OBTAINED BY THIS PROCESS

[75] Inventors: Jacqueline Griat, Ablon; Liliane Ayache, Paris, both of France

[73] Assignee: L'Oreal, Paris, France

[21] Appl. No.: 474,399

[22] Filed: Feb. 6, 1990

[30] Foreign Application Priority Data

Feb. 9, 1989 [LU] Luxembourg ............................ 87.449

[51] Int. Cl.$^5$ .................. A61K 09/122; A61K 09/12; A01N 25/28
[52] U.S. Cl. ...................................... 424/450; 424/47; 424/65; 424/73; 424/76.3; 424/85.8; 424/94.3; 424/92; 424/195.1; 424/401; 424/405; 424/420; 514/945; 264/4.6
[58] Field of Search ...................... 424/450, 43, 45, 47, 424/70, 65, 73, 74, 76.3, 85.8, 92, 94.3, 195.1, 405, 420, 401; 428/402.2; 264/4.1, 4.3, 4.6

[56] References Cited

U.S. PATENT DOCUMENTS

| | | | |
|---|---|---|---|
| 3,811,830 | 5/1974 | DeMarlo | 424/70 X |
| 4,439,342 | 5/1984 | Albanese | 424/46 X |
| 4,608,211 | 8/1986 | Handjani et al. | 264/4.6 |
| 4,772,471 | 9/1988 | Vanlerberghe et al. | 424/450 |
| 4,830,857 | 5/1989 | Handjani et al. | 424/450 |
| 4,839,175 | 6/1989 | Guo et al. | 424/450 |
| 4,897,308 | 1/1990 | Vanlerberghe et al. | 424/450 X |
| 5,021,200 | 6/1991 | Vanlerberghe et al. | 424/450 X |

FOREIGN PATENT DOCUMENTS

| | | |
|---|---|---|
| 0190926 | 8/1986 | European Pat. Off. . |
| 8601714 | 3/1986 | PCT Int'l Appl. . |
| 2189457 | 10/1987 | United Kingdom . |

*Primary Examiner*—Thurman K. Page
*Assistant Examiner*—Neil Levy
*Attorney, Agent, or Firm*—Cushman, Darby & Cushman

[57] ABSTRACT

The invention relates to a process for the preparation of cosmetics or pharmaceutical foam by foaming with the aid of a propellant. According to the invention, a charge consisting of a cosmetics or pharmaceutical product comprising a dispersion of a water-immiscible product in an aqueous solution, the said dispersion being stabilized by niosomes consisting of one or more non-ionic lipid layers encapsulating an aqueous phase, the charge comprising 40 to 95% by weight of dispersion and 5 to 60% by weight of propellant, the proportions being stated with respect to the weight of the total charge of the chamber, are introduced into a chamber which is under pressure and fitted with a valve.

22 Claims, No Drawings

PROCESS FOR THE PREPARATION OF FOAMS WHICH CAN BE USED IN THE COSMETICS AND PHARMACEUTICAL FIELD AND FOAMS OBTAINED BY THIS PROCESS

The present invention relates to a process for the preparation of foams which can be used in the cosmetics and pharmaceutical fields and the foams obtained by this process.

In many cases it is advantageous in the cosmetics or pharmaceutical field to use products in the form of a foam. These are generally easier to apply, because they are less dense and spread more easily.

Foams are generally produced from a liquid phase by the action of a gas. The liquid product to be foamed and a pressurized propellant are introduced into a chamber which is resistant to pressure and is fitted with a valve and a discharge nozzle. The valve is then opened to expel the liquid phase under the action of the pressure generated by the propellant; in the container, the propellant is liquid and is mixed with the liquid product to be distributed to give the liquid phase expelled; on arrival in the atmosphere, the propellant expands and forms a foam, since the product to be distributed has foaming characteristics.

In addition, it is known that certain lipids have the property of forming, in the presence of water, mesomorphous phase in which the state of organization is intermediately between the crystalline state and the liquid state. Amongst the lipids which give rise to mesomorphous phases, it has already been indicated that certain may swell in aqueous solution and form, by stirring, spherules (or vesicles) dispersed in the aqueous medium, these spherules being delimited by multimolecular or bimolecular layers.

French Patents no. 2 315 991, which corresponds to U.S. Pat. No. 4,772,471, and 2 543 018, which corresponds to U.S. Pat. No. 4,608,211 have already described dispersions of spherules or vesicles of lipid in an aqueous phase D; these vesicles are characterized by their leaflet structure consisting of one or more layers of lipid separated from one another by layers of aqueous phase E; they can thus serve to encapsulate water-soluble active substances, for example pharmaceutical or cosmetics substances, and protect them from external conditions. If the lipid compounds used to produce such spherules are ionic compounds they are liposomes, and if they are nonionic compounds they are niosomes.

According to U.S. Pat. No. 4,772,471, these dispersion spherules can be produced by dissolving the respective lipid material in a 2:1 mixture of chloroform and methanol; evaporating the solvent with a rotating evaporator with the last traces thereof being removed by passing the mixture through a blade pump; forming a 3% dispersion of the respective lipid materials in a 0.3M glucose solution, the dispersing operation being conducted at a temperature greater than the crystallization temperature of the lipid material employed; and cooling the resulting dispersion to ambient temperature with agitation.

Thereafter each dispersion, under a nitrogen atmosphere, was subjected to a conventional ultrasonic treatment for a period of 30 minutes at a temperature greater than the crystallization temperature of the lipids. Subsequently, each spherule dispersion was filtered on a column of Sephadex G50 coarse gel swollen in a 9% NaCl saline solution.

U.S. Pat. No. 4,608,211 discloses a process for preparing unilamellar lipid vesicles having an average diameter above 1,000 Å, each of these vesicles consisting of a spheroidal lipid lamella inside which is placed a substance to be encapsulated. The lipid intended to form the lamella of the vesicles is dissolved in at least one water-insoluble solvent. The lipid solution is conditioned in the liquid state, conveniently in a receptacle, at a pressure $P_1$ and at a temperature $\theta_1$. The substance to be encapsulated is dissolved to obtain an aqueous phase. The aqueous phase to be encapsulated is conditioned at a pressure $P_2$ and at a temperature $\theta_2$ and the lipid solution is injected into the aqueous phase so that the solvent of the lipid solution vaporizes on coming into contact with the said aqueous phase. The injection of the lipid solution into the aqueous phase occurs at a low flow rate for instance, a flow rate of 5 ml/hr to 10 ml/minute to form droplets initially. The pressure $P_2$ is less than $P_1$ and less than the vapor pressure of the solvent in the said droplets at temperature $\theta_2$. In a preferred embodiment, $P_1$ is 1–8 bars; $P_2$ is 0.1–15 m bars; and $\theta_1$ and $\theta_2$ are equal to ambient temperature.

French Patents 2 485 921 and 2 490 504 describe the fact that the presence of niosomes stabilizes dispersions of water-immiscible liquids, in particular oil, in the aqueous phase without it being necessary to add an emulsifying agent.

The documents WO 86/01714 and EP-A-O 190 926 describe processes for the preparation of liposomes by spraying the lipid phase under the action of a propellant agent. In WO 86/01714 the lipid phase sprayed is brought into contact with the surface of an aqueous phase to cause formation of the liposomes. In EP-A-O 190 926 the lipid phase is sprayed in solution in an organic solvent combined with water, for example in the form of an emulsion.

The object of the present invention is a process for the preparation of foams which can be used in the cosmetics and pharmaceutical fields, from dispersions of water-immiscible liquids, in particular oils, in water which are stabilized by niosomes.

The present invention relates to a process for the preparation of foams which can be used in the cosmetics or pharmaceutical fields, in which a chamber which is resistant to pressure and is fitted with a valve is charged with a liquid cosmetics or pharmaceutical product, which can form a foam, and a pressurized propellant and the valve is then opened to eject the cosmetics or pharmaceutical product in the form of a foam by expansion of the propellant, characterized in that the pharmaceutical or cosmetics product component used is a dispersion of a water-immiscible phase in an aqueous phase (D) stabilized by niosomes consisting of one or more layers of nonionic lipid compounds encapsulating an aqueous phase (E), this dispersion making up 98 to 40% by weight of the charge of the chamber, the remainder of the charge consisting of 2 to 60% by weight of propellant.

The present invention also relates to the cosmetics or pharmaceutical foam obtained by this process.

The Applicant has discovered that although niosomes are said to be structures which are readily destabilized by solvents of low molecular weight and dispersions stabilized by these niosomes are thus said to be unstable in the presence of these solvents, surprisingly neither the niosomes nor the dispersion are destroyed by the action of the propellant.

According to the invention, the propellant may be a saturated hydrocarbon having 3 or 4 carbon atoms, such as butane, isobutane or propane, or a halogenated hydrocarbon, such as those marketed under the trade name "Freons", or a mixture of these compounds.

The lipids used for the preparation of the niosomes are nonionic amphiphiles of natural or synthetic origin containing one or more long-chain hydrocarbon(s) per molecule. The nonionic lipid compounds used for the preparation of the niosomes are advantageously chosen from the group comprising:

linear or branched polyglycerol ethers of the formulae:

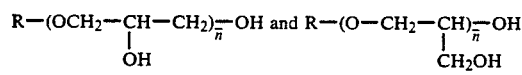

where $\bar{n}$ is an average statistical value of between 2 and 6 and R is a linear or branched aliphatic chain containing 16 to 20 carbon atoms or the hydrocarbon radical of lanoline alcohols;

linear or branched polyglycerol ethers containing two fatty chains;

esters of polyglycerol and linear-chain fatty acids; polyoxyethylene sterols;

glycolipids of natural or synthetic origin, for example the cerebrosides and the $\alpha$- or $\beta$-glucosides of fatty acids.

Various other additives may be combined with the lipid compounds in a known manner in order to modify the permeability or superficial charge of the niosomes. In this respect, there may be mentioned possible addition of long-chain alcohols and diols, sterols, for example cholesterol and $\beta$-sitosterol, long-chain amines and their quaternary ammonium derivatives, in particular dodecyldimethylammonium bromide, bis-hydroxyalkylamines, polyoxyethylene fatty acids or their salts, in particular their quaternary ammonium derivatives, esters of long-chain amino-alcohols and their salts and quaternary ammonium derivatives, phosphoric esters of fatty alcohols, for example sodium dicetyl or dimyristyl phosphate, alkyl sulphates, for example sodium cetyl sulphate, and ionic derivatives of sterols, such as phosphates and sulphates of cholesterol.

It is also possible to add to the lipid compounds forming the spherules at least one lipoprotein chosen from the mono- or polyacylated derivatives of amino acids or polypeptides in which the acyl radical R—CO contains a $C_{13}$-$C_{19}$ hydrocarbon chain, at least one of the functions bonding the polypeptide chain or the amino acid radical to the lipophilic chain being an amide function. The lipoprotein(s) is (or are) present in an amount of 1 to 15% by weight with respect to the total weight of the actual lipid compounds. Lipoproteins which are advantageously used are collagenic palmitoyl-lipoamino-acid, dipalmitoyl-O-N-hydroxyproline acid and hydroxyproline linoleate.

0.5 to 25% by weight of nonionic amphiphile(s), with respect to the total weight of the dispersion of niosomes to be obtained, can advantageously be used to prepare the dispersion of niosomes.

The niosomes used are preferably spherules having an average diameter of between 100 and 50,000 Å, such as those described in French Patent 2 315 991.

It may be anticipated that the aqueous phase E encapsulated in the niosomes is an aqueous solution of the cosmetics or pharmaceutical active substance which is preferably iso-osmotic with respect to the phase D of the dispersion.

For a cosmetics composition, the aqueous phase E encapsulated in the niosomes contains, for example, in dissolved form or in the form of a suspension, at least one product from the group comprising humectants, such as glycerol, sorbitol, pentaerythritol, inositol, pyrrolidone-carboxylic acid and its salts and elastin hydrolysis products; artificial tanning agents, such as dihydroxyacetone, erythrulose, glyceraldehyde and alpha-dialdehydes, such as tartaric aldehyde, if appropriate in combination with colouring agents; water-soluble antisolar agents; antiperspirants; deodorants; astringents; refreshing, tonicizing, cicatrizing, keratolytic and depilatory products; extracts of animal or plant tissues; perfumed water; water-soluble colouring agents; skin removal agents; antiseborrhoeic agents; oxidizing agents, such as hydrogen peroxide, and reducing agents, such as thioglycollic acid and its salts.

In the case of a composition which can be used in pharmacy, the aqueous phase E encapsulated in the niosomes preferably contains at least one product from the group comprising vitamins, hormones, enzymes, such as dismutase superoxide, vaccines, anti-inflammatories, such as hydrocortisone, antibiotics, bactericides, antifungal agents, agents which prevent loss of hair or promote regrowth of hair and retinoids.

In the composition according to the invention, the aqueous phase D surrounding the niosomes contains at least one water-immiscible liquid phase in the form of a dispersion. This water-immiscible liquid phase is preferably an oil.

The oil used, which is to be dispersed in the aqueous phase D, is advantageously chosen from the group comprising esters of fatty acid and polyol, in particular liquid triglycerides, and esters of fatty acid and branched alcohol, of the formula $R_4$—COOR$_5$, in which $R_4$ represents the radical of a higher fatty acid containing 8 to 20 carbon atoms and $R_5$ represents a branched hydrocarbon chain containing 3 to 20 carbon atoms. If the oil is an ester of fatty acid and polyol, it is preferably chosen from the group comprising sunflower, maize, soya, gourd, grape pip, sesame, macadamia, borage and blackcurrant oils and glycerol tricaprocaprylate; if the oil is an ester of a higher fatty acid and branched alcohol, it is preferably Purcellin oil; other vegetable oils can be used, such as, for example, jojoba oil.

The water-immiscible liquid can also be:
a hydrocarbon, such as hexadecane, paraffin oil or perhydrosqualene;
a halogenated hydrocarbon, such as perfluorodecahydronaphthalene;
a polysiloxane;
an ester of an organic acid;
an ether or a polyether;
or perfluorotributylamine.

It can also be anticipated that the aqueous phase D which surrounds the niosomes contains at least one adjuvant chosen from the group comprising opacifying agents, gelling agents, flavouring agents, water-soluble solar filters and colouring agents. The adjuvants are liposoluble and can be dissolved in the water-immiscible oil dispersed in the aqueous phase D. If this water-immiscible liquid is to contain dissolved adjuvants, these adjuvants are preferably dissolved before the dispersing operation is performed.

Such adjuvants can be, for example, liposoluble solar filters, such as 2-ethylhexyl paradimethylaminobenzoate, perfumes or substances for improving the condition of dry or geriatric skin, in particular non-saponifiable substances, such as non-saponifiable products of soya, avocado, tocopherols, vitamins E and F and antioxidants.

The non-liposoluble additives are generally added to the preparation after dispersion of the oil. The gelling agent may be introduced in a concentration whch varies between 0.1 and 2%, these percentages being expressed by weight with respect to the total weight of the composition. Amongst the gelling agents which can be used there may be mentioned cellulose derivatives, such as hydroxyethylcellulose; algae derivatives, such as those sold under the trade name "Satiagum"; or naturally occurring gums, such as gum tragacanth. The gelling agent which is preferably used is hydroxyethylcellulose, a mixture of vinylcarboxylic acids commercially available under the name "CARBOPOL 940", the product sold under the trade name "Satiagum" or gum tragacanth.

The aqueous phase D of the dispersion of niosomes and/or the internal aqueous phase E of the niosomes can also contain a dissolved water-soluble polyamide polymer having a molecular weight of between 1,000 and 200,000, the concentration of which is 0.01 to 5% by weight with respect to the total weight of the composition. Polyamide polymers which may be mentioned are polyacrylamide, poly-beta-alanine, poly(glutamic acid). polytyrosine, polylysine and poly(aspartic acid), and proteins, such as alphalactalbumin, serum albumin, lactic hydrolysis products, hydrolysis products of collagen and hydrolysis products of gelatine.

Any of the processes previously known and described can be used to obtain the dispersion of the lipid spherules in the aqueous phase D.

It is possible to use, for example, the process which comprises dissolving the lipids in a volatile solvent, forming a thin film of lipids on the walls of a flask by evaporation of the solvent, introducing the aqueous phase E into the said flask, encapsulating, and stirring the mixture mechanically until the dispersion of spherules of desired size is obtained; in this case, the aqueous phases D and E are necessarily identical.

It is also possible to use to the process described in French Patent no. 2 315 991. This process is particularly suitable if the use of multilamellar spherules is desired.

In the case where unilamellar spherules are desired, the process described in French Patent no. 2 543 018 can be used for their preparation.

The examples given below purely for illustration and non-limitatively are for better understanding of the invention.

PREPARATION OF A DISPERSION A

A first dispersion A consisting of a dispersion of oil in an aqueous phase is prepared, the said dispersion being stabilized by niosomes.

First phase

The process described in French Patent no. 2 315 991 is used to obtain a dispersion of niosomes in an aqueous phase starting from the following formulation:

Non-ionic amphiphilic lipid of the formula:

| | |
|---|---|
| $R-(OCH_2-CH)_{\bar{n}}-OH$ <br> $\phantom{R-(OCH_2-}CH_2OH$ | 3.6 g |
| in which formula R is a hexadecyl radical and $\bar{n}$ has an average statistical value equal to 3 | |
| Cholesterol | 3.6 g |
| Collagenic palmitoyl acid | 0.8 g |
| Methyl parahydroxybenzoate | 0.3 g |
| Glycerol | 3.0 g |
| Demineralized water | 35.5 g |

A dispersion of niosomes having an average diameter of 10,000 Å is obtained.

Second phase 15 g sesame oil and 0.4 g perfume are added to the mixture thus obtained. The entire mixture is stirred mechanically until a very fine homogeneous dispersion is obtained, as previously disclosed, for instance, in French patent application No. 80 2499, publication No. 2 490 504 wherein it is stated that the dispersion of the water-immiscible liquid phase (or phases) is advantageously produced with the acid of an ultra-disperser, at a temperature in the region of ambient temperature, which represents a significant advantage from the economic point of view, for the stability of the constituents of the composition, in particular if they are volatile or oxidizable, and for safety. The average diameter of the droplets of the water-immiscible liquid is from 0.1 to a few microns.

The following substances are finally added:

| | |
|---|---|
| Polyvinylcarboxylic acid marketed under the name "CARBOPOL 940" | 0.4 g |
| Triethanolamine | 0.4 g |
| Demineralized water | 37.0 g |

PREPARATION OF A DISPERSION B

A second dispersion B is prepared by the same process starting from the following formulation:

Non-ionic amphiphilic lipid of the formula:

| | |
|---|---|
| $C_{12}H_{25}-O$ <br> $\phantom{C_{12}H_{25}-}\|$ <br> $\phantom{C_{12}H_{25}-}CH_2$ <br> $\phantom{C_{12}H_{25}-}\|$ <br> $R'-CH-O-(CH_2-CH-O)_{\bar{n}}-H$ <br> $\phantom{R'-CH-O-(CH_2-}\|$ <br> $\phantom{R'-CH-O-(CH_2-}CH_2OH$ | 0.95 g |
| where R' represents a mixture of radicals $C_{14}H_{24}$ and $C_{16}H_{33}$ and $\bar{n}$ is an average statistical value equal to 6 | |
| Dimyristyl phosphate | 0.05 g |
| Methyl parahydroxybenzoate | 0.3 g |
| Glycerol | 3 g |
| Hydroxyproline | 1 g |
| Elastin hydrolysis products | 3 g |
| Demineralized water | 35.5 g |

The following substances are then added to the dispersion of niosomes obtained:

| | |
|---|---|
| Macadamia oil | 15 g |
| Tocopherols | 0.2 g |
| Perfumes | 0.4 g |

The entire mixture is stirred mechanically until a very fine homogeneous dispersion is obtained.

The following substances are finally added to the dispersion:

| | |
|---|---|
| Polyvinylcarboxylic acid marketed under the name "CARBOPOL 940" | 0.4 g |
| Triethanolamine | 0.4 g |
| Demineralized water | 39.6 g |

EXAMPLES 1 TO 5

Dispersions A or B prepared as described above are introduced as the batch into a pressurized container together with one of the four following propellant gases:

| Propellant symbol | Composition of the mixture forming the propellant |
|---|---|
| $P_1$ | butane/propane/isobutane (25/20/55) |
| $P_2$ | difluoro-dichloro-methane |
| $P_3$ | difluoro-dichloro-methane/dichloro-tetrafluoroethane (50/50) |
| $P_4$ | $P_1$/dichlorotetrafluoroethane (30/70) |

The following five examples corresponding to the use of the process according to the invention are carried out:

| Example no. | Propellant Nature | Propellant Amount | Dispersion Nature | Dispersion Amount |
|---|---|---|---|---|
| 1 | $P_1$ | 30 | A | 70 |
| 2 | $P_2$ | 30 | A | 70 |
| 3 | $P_1$ | 30 | B | 70 |
| 4 | $P_3$ | 30 | B | 70 |
| 5 | $P_4$ | 30 | B | 70 |

These amounts are given in % by weight with respect to the total batch

It is found in all cases that the foams obtained contain niosomes which have thus existed in the presence of the propellant and continue to have their stabilizing action on the dispersions in the foams.

EXAMPLE 6

A batch containing 98% by weight of the dispersion A and 2% by weight of a propellant consisting of a mixture of propane, isobutane and n-butane (10/50/40) was prepared.

The batch was kept at room temperature for 6 months and the presence of niosomes was verified by ultrastructural examination under an electron microscope by the cryofracture technique. It was found that the batch contains niosomes having diameters of between 80 and 300 nm.

EXAMPLE 7

The batches of examples 4 and 5 were kept for 8 months and the presence of niosomes was verified by the process described in example 6. The presence of numerous niosomes having a diameter of between 50 and 200 nm in the case of the batch from example 4 and niosomes having a diameter of between 150 and 400 nm in the case of the batch from example 5 were found.

EXAMPLE 8

A batch containing 70% by weight of dispersion B and 30% by weight of a propellant consisting of a mixture of butane-propane-isobutane-pentane (68.2/8/22/1.8) was prepared. This batch was kept at room temperature for 8 months and the presence of niosomes was verified by the process described in example 6. The presence of a large number of niosomes having a diameter of between 200 and 300 nm was found.

We claim:

1. A process for preparing a cosmetic or pharmaceutical foam comprising
charging a pressure resistant chamber fitted with a valve with a foamable liquid cosmetic or pharmaceutical product and a pressurized propellant,
opening the valve thereby discharging said cosmetic or pharmaceutical product from said chamber as a result of expansion of said propellant in the form of a foam,
said cosmetic or pharmaceutical product comprising a dispersion of a water-immiscible phase dispersed in an aqueous medium stabilized with niosomes comprising one or more layers of a nonionic lipid compound encapsulating an aqueous phase, said dispersion constituting 98 to 40 percent by weight of the charge in said chamber, the remainder being said propellant.

2. The process of claim 1 wherein said propellant is selected from the group consisting of a saturated hydrocarbon having 3–4 carbon atoms, a halogenated hydrocarbon and a mixture thereof.

3. The process of claim 1 wherein said lipid compound is a natural or synthetic nonionic amphiphile containing at least one long-chain hydrocarbon per molecule.

4. The process of claim 1 wherein said nonionic lipid compound is selected from the group consisting of
(a) a linear or branched polyglycerol ether having the formula

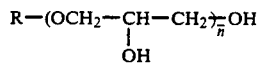

or the formula

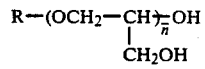

wherein
$\bar{n}$ has an average statistical value between 2 and 6 and
R is a linear or branched aliphatic chain having 16 to 20 carbon atoms or the hydrocarbon radical of a lanolin alcohol,
(b) a linear or branched polyglycerol ether containing two fatty chains,
(c) an ester of polyglycerol and a linear chain fatty acid,
(d) a polyoxyethylene sterol, and
(e) a natural or synthetic glycolipid.

5. The process of claim 1 wherein said nonionic lipid compound is present in an amount ranging from 0.5 to 25 percent by weight based on the total weight of said dispersion.

6. The process of claim 1 which includes adding to said nonionic lipid compound forming said niosomes at least one compound selected from the group consisting of a long chain alcohol, a long chain diol, a sterol, a long chain amine, a bishydroxyalkyl amine, a polyoxyethylene amine, an ester of a long chain amino alcohol or a salt thereof or a quaternary ammonium derivative thereof, a phosphoric ester of a fatty alcohol, an alkyl sulphate and an ionic derivative of a sterol.

7. The process of claim 1 which includes adding to said nonionic lipid compound forming said niosomes at least one lipoprotein selected from the group consisting of a mono- or polyacylated derivative of an amino acid or polypeptide in which the acyl radical R—CO contains a $C_{13}$-$C_{19}$ hydrocarbon chain, at least one of the functions bonding the polypeptide chain or amino acid radical to the lipophilic chain being an amide function.

8. The process of claim 7 wherein said lipoprotein is selected from the group consisting of collagenic palmitoyl lipoamino acid, dipalmitoyl-O-N-hydroxyproline acid and hydroxyproline linoleate.

9. The process of claim 1 wherein the aqueous phase encapsulated in said niosomes contains at least one product selected from the group consisting of a humectant, an artificial tanning agent, an antiperspirant, a deodorant, an astringent, a refreshing agent, a tonic agent, a cicatrizing agent, a keratolytic agent a depilatory agent, an extract of an animal or plant tissue, perfumed water, a water-soluble coloring agent, a skin removal agent, an antisolar agent, an antiseborrheic agent, an oxidizing agent and a reducing agent.

10. The process of claim 1 wherein the aqueous phase encapsulated in said niosomes contains at least one product selected from the group consisting of a vitamin, a hormone, an enzyme, a vaccine, an anti-inflammatory agent, an antibiotic, a bactericide, an antifungal agent, an agent to prevent hair loss, an agent to promote hair growth and a retinoid.

11. The process of claim 1 wherein said water-immiscible phase dispersed in said continuous aqueous medium is an oil.

12. The process of claim 11 wherein said oil is selected from the group consisting of an ester of a fatty acid and a polyol and an ester of a fatty acid and a branched alcohol, having the formula $R_4$—$COOR_5$ wherein $R_4$ represents the radical of a higher fatty acid containing 8 to 20 carbon atoms and $R_5$ represents a branched hydrocarbon chain containing 3 to 20 carbon atoms.

13. The process of claim 11 wherein said oil is an ester of a fatty acid and a polyol and is selected from the group consisting of sunflower oil, maize oil, soya oil, gourd oil, grape pip oil, black currant oil, sesame oil, macadamia oil, borage oil and glycerol tricaprylate.

14. The process of claim 11 wherein said oil is Purcellin oil.

15. The process of claim 1 wherein said water-immiscible phase dispersed in said continuous aqueous medium is selected from the group consisting of a hydrocarbon, a halogenated hydrocarbon, a polysiloxane, an organic acid ester, an organic acid ether, an organic acid polyether and perfluorotributylamine.

16. The process of claim 1 wherein said continuous aqueous medium contains a gelling agent.

17. The process of claim 16 wherein said gelling agent is selected from the group consisting of a cellulose derivative, an algae derivative, a naturally occurring gum and a mixture thereof.

18. The process of claim 1 wherein one or both of continuous aqueous medium and said aqueous phase encapsulated in said niosomes contains at least one water-soluble polyamide polymer dissolved therein, said water-soluble polyamide polymer having a molecular weight ranging from 1,000 to 200,000 and is present in an amount ranging from 0.01 to 5 percent by weight based on the total weight of said dispersion distributed in the form of a foam.

19. The process of claim 18 wherein said water-soluble polyamide polymer is selected from the group consisting of polyacrylamide, poly-beta-alanine, poly (glutamic acid), polytryosine, polylysine and poly (aspartic acid).

20. The process of claim 18 wherein said water-soluble polyamide polymer is selected from the group consisting of alphalactalbumin, serum albumin, a lactic acid hydrolysis product, a hydrolysis product of collagen or a hydrolysis product of gelatin.

21. The process of claim 1 wherein said water-immiscible phase is added to said continuous aqueous medium, the resulting mixture is intensively stirred and thereafter the stirred mixture is admixed with said propellant.

22. A foam obtained in accordance with the process of claim 1.

* * * * *